United States Patent

Hyde et al.

[11] Patent Number: 5,958,789
[45] Date of Patent: Sep. 28, 1999

[54] REDUCTION IN POSITIVE BIAS IN WET ASSAYS DUE TO SPLASHING

[75] Inventors: David Donald Hyde, Ontario; Merrit Nyles Jacobs, Fairport; James Daniel Riall, Pittsford, all of N.Y.

[73] Assignee: Johnson & Johnson Clinical Diagnostics, Inc., Rochester, N.J.

[21] Appl. No.: 08/902,463

[22] Filed: Jul. 29, 1997

[51] Int. Cl.[6] .................................................. G01N 33/53
[52] U.S. Cl. .............................. 436/500; 422/63; 422/67; 436/43; 436/47; 436/65; 436/510; 436/815; 436/817; 436/818
[58] Field of Search .............................. 422/63, 67, 100; 436/500, 510, 43, 47, 65, 815, 817, 818

[56] References Cited

U.S. PATENT DOCUMENTS 5,443,791  8/1995  Cathcart et al. ........................... 422/65
5,525,302  6/1996  Astle ........................................ 422/100

*Primary Examiner*—Christopher L. Chin
*Attorney, Agent, or Firm*—Dana M. Schmidt

[57] ABSTRACT

A method of preventing false detection of signal due to splashing of reagent liquid used to produce such signal, when dispensing at least one such liquid from a metering tip into a second liquid, comprising the steps of:

a) positioning the metering tip a predetermined distance above the upper level of the second liquid prior to dispensing the one liquid; and b) while maintaining the distance throughout the dispensing of the one liquid, dispensing the one liquid;

wherein the predetermined distance is between about 1.0 mm and about 2.0 mm so that splashing during dispensing is reduced.

5 Claims, 1 Drawing Sheet

REDUCTION IN POSITIVE BIAS IN WET ASSAYS DUE TO SPLASHING

FIELD OF THE INVENTION

This invention relates to a process for conducting wet assays during which at least one analyte-specific liquid reagent is added to a sample liquid prior to incubation and the washing out of unbound reagent. More specifically, it concerns a method for reducing the detection of unbound reagent that surprisingly has not been removed by conventional washing.

BACKGROUND OF THE INVENTION

It is known to induce a chemiluminescent reaction between a signal reagent and a liquid analyte such as TSH, by conducting the following steps in a container with walls bearing a coating of avidin:

a) positioning the metering tip a predetermined distance above the upper level of the liquid analyte prior to dispensing a labeled liquid reagent specific to the TSH, that is, an antibody to the TSH labeled with horseradish peroxidase (hereinafter, HRP);

b) while maintaining the distance throughout the dispensing of the liquid reagent, dispensing that reagent;

c) repeating steps a) and b) for a second liquid reagent, for example one capable of reacting with both the TSH and the container wall, e.g., an antibody to TSH that is bound to biotin;

d) incubating the liquids present in the container for a time sufficient to bind the labeled reagent to any of the TSH present in the sample, and the TSH to the container;

e) washing out unbound amounts of the labeled reagent from the container by i) removing the liquids therefrom, ii) adding wash fluid back to the container, and iii) repeating steps i) and ii) at least once; and f) adding the signal reagent to induce chemiluminescence. The known process uses dispensing heights (the predetermined distances) that range from 8.34 mm at the maximum to 5.58 mm at the minimum.

This process works generally quite well with most analytes. However, with TSH, it has been discovered that outliers can result that produce a positive bias. Because the containers are thoroughly washed to remove free labeled reagent, that is, reagent unbound through the analyte to the container, it was not at all clear what the cause was for this problem. Extensive modifications were attempted without success.

As used herein, "unbound" reagent refers to reagent that is not immobilized to the container through a conventional attachment process, such as a sandwich assay involving the analyte and an immobilized analyte-specific reagent. Such unbound reagent can be complexed with analyte not complexed with the immobilizing analyte-specific reagent. In this latter case, the complex of label reagent and analyte is conventionally removed by the wash process—hence it is considered "unbound".

Thus, there has been a need for a solution to the positive bias occasionally produced in TSH analysis.

SUMMARY OF THE INVENTION

The problem has been solved by the unexpected discovery of the cause of the problem. That is, we discovered that the wash step has been ineffective apparently because, unexpectedly, the unbound labeled reagent specific to TSH (the antibody bonded to HRP), when splashed onto the container walls above the bulk liquid in the container, attaches firmly to the container wall during the incubation step so as to be at least partly unremovable during washing. It is not so much that splashing was unexpected, but that all the reagent so splashed was not removed during washing.

The solution then was to alter the dispensing height to reduce the splashing and thus the reagent deposited above the bulk liquid.

More specifically, in accord with one aspect of the invention, there is provided a method of preventing false detection of signal due to splashing of reagent liquid used to produce such signal, when dispensing at least one such liquid from a metering tip into a second liquid, comprising the steps of:

a) positioning the metering tip a predetermined distance above the upper level of the second liquid prior to dispensing the one liquid; and b) while maintaining the distance throughout the dispensing of the one liquid, dispensing said one liquid;

wherein the predetermined distance is between about 1.0 mm and about 2.0 mm so that splashing during dispensing is reduced.

In accord with another aspect of the invention, there is provided a method of preventing false readings of thyroid stimulating hormone (TSH) analyte using a labeled analyte-specific liquid reagent that is added to a container to which liquid sample is also added for reaction, and a detection of the reagent reacted with the sample following a wash treatment to remove unreacted reagent from the container. The method comprises the steps of:

a) dispensing from a tip an amount of the labeled analyte-specific reagent for delivery into the sample liquid in the container, while maintaining throughout the dispensing, the height of the tip from the sample liquid a first predetermined distance;

b) optionally adding on additional reagent to the sample liquid intermixed in the container with the liquid reagent added in step b), by dispensing from a tip the optional additional reagent all while maintaining the height of the tip from the liquid in the container at a second predetermined distance, at least one of the reagents being capable of binding to the container;

c) incubating the liquids present in the container for a time sufficient to bind the labeled reagent to any of the TSH present in the sample, and the TSH to the container;

d) washing out unbound amounts of the label reagent from the container by i) removing the liquids therefrom, ii) adding wash fluid back to the container, and iii) repeating steps i) and ii) at least once;

e) adding a signal reagent to the container effective to react with the bound labeled reagent to produce a detectable result; and f) detecting the result;

wherein the predetermined maintained distances are reduced to a value of from between about 1.0 mm to about 2.0 mm, so that splashing of the labeled reagent out of the liquid onto the container walls where it becomes irretrievably bound during step c), is reduced.

Accordingly, it is an advantageous feature of the invention that outliers having a positive bias are avoided or minimized in a wet assay.

It is a related advantageous feature of the invention that the outliers are minimized without having to immerse the dispensing tip into the sample liquid (which would risk carry-over contamination).

Other advantageous features will become apparent upon reference to the Detailed Description of the Preferred Embodiments, when viewed in light of the attached drawings.

DETAILED DESCRIPTION OF THE PREFERRED EMBODIMENTS

The invention is described in connection with certain preferred embodiments, wherein a particular container is described along with a preferred analyzer for conducting a wet assay for TSH. In addition, the invention is useful with other containers and analyzers, and other wet assays besides TSH, especially those producing a low level of signal in the normal range of analytes, for example, hCG. Thus, the actual liquid added in the process may vary, depending on the assay that is run.

Thus, FIGS. 1A–1H, a preferred container is the type shown in U.S. Pat. No. 5,441,895, and a preferred analyzer for processing such a container is that shown in, e.g., U.S. Pat. No. 5,518,693 (wherein the containers are also called cuvettes C).

The process illustrated by the Figures will first be described in connection with the prior art. The process remains the same for the invention, except that the tip height is changed from "$H_O$" to "$H_N$".

Figure 1A:
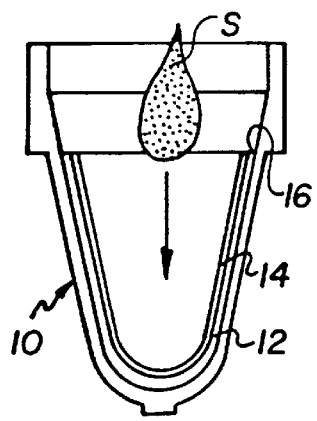
FIGS. 1A–1H are partially schematic elevational views in section of a container of liquid and the dispensing and aspirating tips used therewith illustrating both the prior art process and the new process of the invention.

Container 10 as supplied, FIG. 1A, has a coating 12 of strep-avidin forming a top edge 16, and over layer 12, a dried layer 14 of a suitable sugar. The first step in the actual assay is to add a quantity, such as 80 $\mu$L, of sample "S" from a suitable dispenser (not shown), to produce that state shown in FIG. 1B where the sugar, but not the strep-avidin layer 12, has dissolved.

Figure 1B:
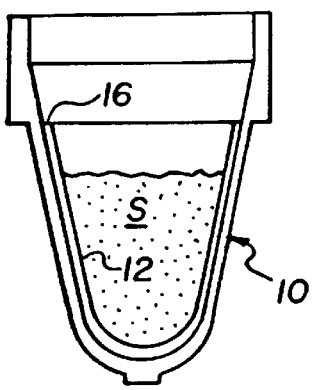

Next, FIG. 1B, a second liquid $R_1$ is added to the first liquid S. Preferably, this comprises a labeled analyte-specific reagent, such as a labeled antibody for the analyte of choice in sample S. For example, in the case of TSH, $R_1$ is a monoclonal antibody against TSH labeled with horse-radish peroxidase, hereinafter, HRP. Most preferably, $R_1$ is about 20 $\mu$L, dispensed from a tip 20 at a certain height. Conventionally that height has been $H_O$ which varies from between about 8.34 mm to about 7.56 mm. That is, since the tip 20 and container 10 are fixed, $H_O$ decreases as $R_1$ is added.

Figure 1C:
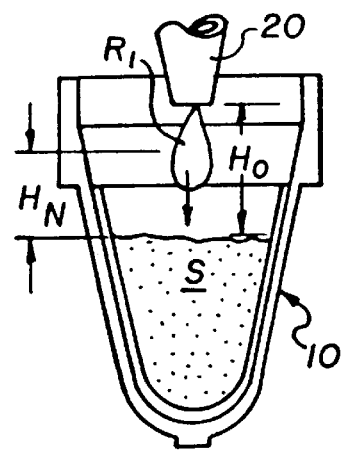
Figure 1D:
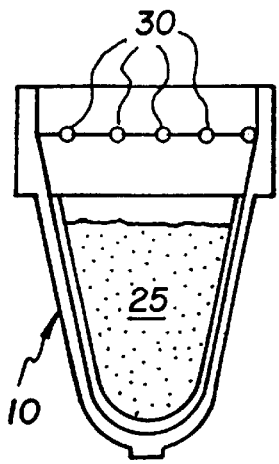

The result appears in FIG. 1D. Because of the height $H_O$, minute droplets 30 of $R_1$ are splashed up above the bulk amount of mixed liquid 25 now present in container 10. These collect primarily at lip 32 formed as part of the molding process for container 10, but can also collect elsewhere on the walls (not shown) above liquid 25.

Figure 1E:
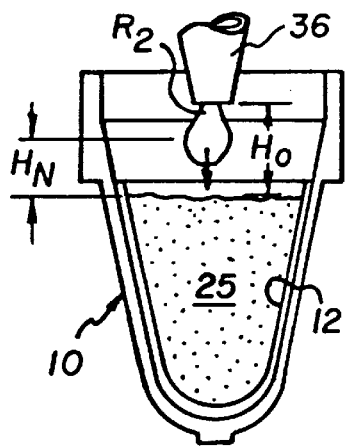

Next, FIG. 1E, a second reagent $R_2$ is optionally added from a tip 36, again at a conventional height $H_O$. For example, $R_2$ can be an analyte-specific reagent bound to an immobilizing moiety. Because of the coating 12 on container 10, most preferably $R_2$ comprises an antibody against TSH attached to biotin. Most preferably, the amount of $R_2$ is about 60 $\mu$L, and conventionally, $H_O$ starts out at about 7.56 mm and decreases to about 5.58 mm as $R_2$ is added.

Figure 1F:
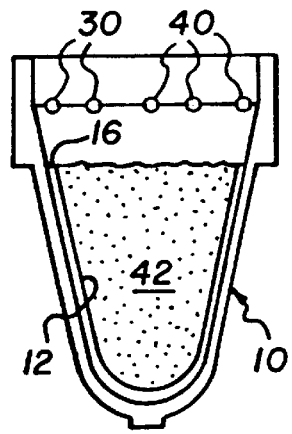

The result appears in FIG. 1F. Additional droplets of $R_1$ (and possible $R_2$) appear at 30 and 40 due to splashing occurring from the use of height $H_O$ in FIG. 1E. Liquid 42 is a mixture of sample and reagents $R_1$ and $R_2$, and at this stage, a long period of incubation occurs, that lasts preferably for at least 15 minutes. For TSH, incubation is about 30 minutes. In the process described, during this time a sandwich assay occurs wherein TSH (if present) in the sample complexes with $R_1$ and $R_2$, and $R_2$ bonds to layer 12 of container 10.

More importantly, we have discovered that droplets 30,40 dry and firmly attach during incubation to the wall of container 10 above bulk liquid 42. Surprisingly, this attachment is such that subsequent washing, described hereinafter, apparently does not remove the droplets, contrary to conventional wisdom regarding washing of "unbound" reagents, that is, analyte-specific reagents that have not complexed with properly immobilized sample. ($R_1$ may in fact be complexed with TSH in droplets 30, but these would not be expected to be immobilized because there is no avidin above the top edge 16 of layer 12 for the TSH to attach to via any $R_2$ reagent from droplets 40.)

Figure 1G:
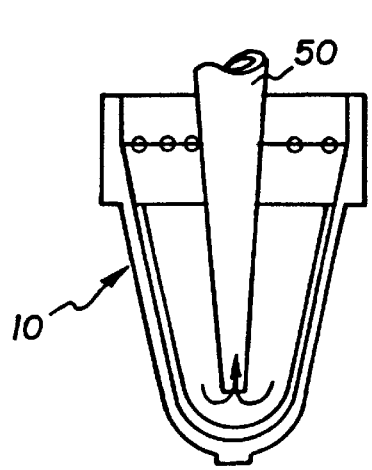
Figure 1H:
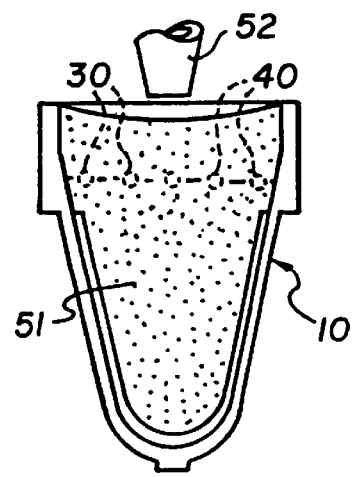

In any event, subsequently, FIG. 1G, the process proceeds by removing from container 10 through aspirating tip 50, all liquid, and then filling container 10, FIG. 1H, by adding a wash 51 from tip 52 all the way to the top of the container, as shown. It was expected from conventional wisdom that this would wash away any droplets such as those formed previously at 30 and 40. However, we have discovered that significant amounts of those remain as shown in phantom, FIG. 1H.

Thus, in the remaining wash steps, not shown, when tip 50 or the equivalent is used to aspirate out "all" the liquid, we have discovered that droplets 30 and 40 remain behind. Amazingly, this is true even though the steps of FIGS. 1H and 1G are repeated several times. That is, the wash is not completed until emptying out, FIG. 1G, and adding back wash liquid, FIG. 1H, occurs three or four times in a row.

Following washing, a conventional signal reagent is added (not shown) that reacts with the peroxidase to produce a detectable result, for example, chemiluminescence, which is then detected by a suitable, conventional reader (also not shown).

Tip Height

Having made our discovery of the cause of the problem being the performance of droplets 30,40, the improvement resides then in drastically altering $H_O$ to a new value of $H_N$ so as to reduce substantially the tendency to cause splashing in the steps of FIGS. 1C and 1E. More precisely, the tip height is reduced to a value $H_N$, FIGS. 1C and 1E, which is in the range of about 1.0 mm to about 2.0 mm. Additionally, that tip height $H_N$ is preferably rendered constant during all dispensing of $R_1$ (and $R_2$ if used), by "tracking" the tip. That is, as $R_1$ is added, FIG. 1C, and as the liquid height of container 10 increases, tip 20 is moved up correspondingly, by conventional algorithms, to maintain $H_N$ constant. Alternatively, the height need not be constant above the liquid, but instead it can decrease as liquid is added, so long as the height remains within the range of about 1 to about 2 mm.

If tip height $H_N$ is reduced below about 1.0 mm, there is a risk that it will contact the bulk liquid so that the tip will become contaminated. The disadvantage of using a value of $H_N$ that is greater than about 2.0 mm is that the reduction in splashing decreases at such greater heights.

It should be noted that $H_N$ can be exactly the same for the dispensing of both $R_1$ and $R_2$, or $H_N$ can be different for each, but still be within the range of about 1 mm to about 2 mm.

Dispense Rate

A further improvement in the reduction of splashing has been made by altering the dispense rate out of tips 20 and 36. Such tips have an orifice diameter of about 0.5 mm. Conventionally the dispense rate has been about 330 $\mu$L/sec. However, I have made the unexpected discovery that increasing the rate to about 380 $\mu$L/sec further reduces splashing. That this is unexpected can be seen from the fact that the increased rate increases the momentum of the incoming liquid, and conventional wisdom holds that increasing such momentum will cause more splashing, not less. For example, U.S. Pat. No. 5,525,302, column 4, lines 59–61 state "If the speed [of delivery of liquid from a pipette tip] is too fast, the stream will have too much energy and bounce or splash from its intended receptacle." However, high speed motion pictures of the event in this invention prove that the reverse is the case, at least in this instance.

Alternate Embodiment

As indicated above, $R_2$ is an optional reagent. For example, coating 12 could alternatively comprise an antibody against the analyte (here, TSH) that is immobilized on container 10. In such a case, $R_2$ would not be needed since sample S would attach to the container after it is added in step 1A. The labeling reagent $R_1$, however would still be needed.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of preventing false detection of signal due to splashing of reagent liquid used to produce such signal, when dispensing at least one such liquid from a metering tip into a second liquid having an exposed upper level, comprising the steps of:

a) positioning the metering tip a predetermined distance above the upper level of the second liquid prior to dispensing the one liquid; and b) while maintaining said distance throughout the dispensing of the one liquid, dispensing said one liquid;

wherein said predetermined distance is between about 1.0 mm and about 2.0 mm so that splashing during dispensing is reduced.

2. A method as defined in claim 1, wherein all additional liquids are dispensed into liquids already present, using said predetermined distance.

3. A method as defined in claim 1, wherein said step b) comprises dispensing said one liquid out of an orifice of about 0.5 mm diameter at a rate of about 380 $\mu$L per sec to further reduce splashing.

4. A method as defined in claim 1, wherein said reagent liquid is a labeled analyte-specific reagent used in a wet immunoassay.

5. A method as defined in claim 4, wherein said immunoassay is selected from the group consisting of TSH and hCG.

* * * * *